(12) United States Patent
Roe et al.

(10) Patent No.: US 12,311,161 B2
(45) Date of Patent: May 27, 2025

(54) RECTIFIER AND THE TIMING OF SWITCHING OF CAPACITORS

(71) Applicant: Boston Scientific Scimed, Inc., Maple Grove, MN (US)

(72) Inventors: Jacob A Roe, North St. Paul, MN (US); Jonathan P. Roberts, Coon Rapids, MN (US); Joel B. Artmann, Elk River, MN (US); David J. Peichel, Minneapolis, MN (US); Michael Kemmerer, Victoria, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 860 days.

(21) Appl. No.: 17/462,905

(22) Filed: Aug. 31, 2021

(65) Prior Publication Data

US 2022/0062620 A1 Mar. 3, 2022

Related U.S. Application Data

(60) Provisional application No. 63/072,440, filed on Aug. 31, 2020.

(51) Int. Cl.
*A61M 60/873* (2021.01)
*A61M 60/148* (2021.01)

(52) U.S. Cl.
CPC ........ *A61M 60/873* (2021.01); *A61M 60/148* (2021.01); *A61M 2205/8206* (2013.01); *A61M 2205/8243* (2013.01)

(58) Field of Classification Search
CPC .............. A61M 60/873; A61M 60/148; A61M 2205/8206; A61M 2205/8243;
(Continued)

(56) References Cited

U.S. PATENT DOCUMENTS 4,613,937 A * 9/1986 Batty, Jr. ................. G06F 21/71
607/31
6,478,820 B1 * 11/2002 Weiss ................... A61M 60/873
623/3.27

(Continued)

OTHER PUBLICATIONS

International Search Report and Written Opinion of International Application No. PCT/US2021/048369, dated Feb. 7, 2022, 10 pp.

*Primary Examiner* — Daniel Kessie
*Assistant Examiner* — Brian K Baxter
(74) *Attorney, Agent, or Firm* — Seager Tufte & Wickhem, LLP

(57) ABSTRACT

An internal coil interface implantable within the body of a patient and configured to modulate a load on an internal coil, and a method therefore are provided. According to one aspect, processing circuitry of the internal coil interface is configured to predict a time of a first voltage level crossing by a voltage at a terminal of the internal coil for each of a plurality of successive windows each time the capacitance is switched into the modulated load circuit or each time the capacitance is switched out of the modulated load circuit. The process is also configured to adjust the predictions based on whether a previous prediction of a time of a first voltage level crossing for a window was later or earlier than a time at which the first voltage level crossing actually occurred.

20 Claims, 12 Drawing Sheets

(58) Field of Classification Search
CPC ........ H02J 2310/23; H02J 50/12; H02J 50/80; H02M 7/217; A61N 1/3605
See application file for complete search history.

(56) References Cited

U.S. PATENT DOCUMENTS

| | | | |
|---|---|---|---|
| 7,191,007 B2 | 3/2007 | Desai et al. | |
| 7,286,880 B2 | 10/2007 | Olson et al. | |
| 8,608,635 B2 | 12/2013 | Yomtov et al. | |
| 8,797,771 B1* | 8/2014 | Lee | H02M 7/103 363/63 |
| 8,974,366 B1 | 3/2015 | Radziemski et al. | |
| 9,192,704 B2 | 11/2015 | Yomtov et al. | |
| 9,504,775 B2 | 11/2016 | Yomtov et al. | |
| 9,608,537 B1* | 3/2017 | Lee | H02M 1/0045 |
| 9,680,310 B2 | 6/2017 | Wong et al. | |
| 9,717,917 B2* | 8/2017 | Dellamano | H02J 50/40 |
| 9,770,544 B2 | 9/2017 | Yomtov et al. | |
| 10,137,232 B2 | 11/2018 | Yomtov et al. | |
| 10,177,645 B2* | 1/2019 | Tao | H02M 1/08 |
| 10,376,624 B2* | 8/2019 | Rudser | A61M 60/875 |
| 10,413,651 B2 | 9/2019 | Yomtov et al. | |
| 10,432,107 B2* | 10/2019 | Yamada | H02M 1/08 |
| 10,476,400 B1* | 11/2019 | Le | H02J 50/12 |
| 10,505,396 B2* | 12/2019 | Iwasaki | H02J 50/80 |
| 10,644,531 B1* | 5/2020 | Qiu | H02J 50/10 |
| 10,840,742 B2* | 11/2020 | de Rooij | H02J 50/12 |
| 11,031,818 B2* | 6/2021 | Danilovic | H02H 3/38 |
| 11,409,381 B2* | 8/2022 | Lee | G06F 3/03545 |
| 11,547,862 B2* | 1/2023 | Winstrom | A61N 1/3787 |
| 11,581,756 B2* | 2/2023 | Mynar | H02J 50/60 |
| 2002/0087204 A1 | 7/2002 | Kung et al. | |
| 2005/0288739 A1 | 12/2005 | Hassler, Jr. et al. | |
| 2010/0211134 A1* | 8/2010 | Forsell | A61N 1/08 607/61 |
| 2010/0222848 A1* | 9/2010 | Forsell | H02J 50/10 607/61 |
| 2013/0099585 A1* | 4/2013 | Von Novak | H02J 50/12 307/104 |
| 2013/0235635 A1* | 9/2013 | Takahagi | H02J 7/02 363/127 |
| 2013/0238048 A1* | 9/2013 | Almendinger | A61N 1/0509 607/40 |
| 2013/0289334 A1* | 10/2013 | Badstibner | H01F 38/14 307/104 |
| 2014/0043003 A1* | 2/2014 | Lee | G05F 1/10 323/283 |
| 2014/0071725 A1* | 3/2014 | Orr | H02M 1/4208 363/89 |
| 2014/0265621 A1 | 9/2014 | Wong et al. | |
| 2014/0266019 A1* | 9/2014 | Pigott | H02J 50/80 320/108 |
| 2015/0080639 A1 | 3/2015 | Radziemski et al. | |
| 2015/0137610 A1* | 5/2015 | Kohout | H02J 50/10 307/104 |
| 2015/0207338 A1* | 7/2015 | Uchimoto | H02J 50/10 307/104 |
| 2015/0290373 A1* | 10/2015 | Rudser | A61M 60/538 623/3.27 |
| 2015/0357899 A1* | 12/2015 | Ekbote | H02M 1/4225 323/284 |
| 2016/0011611 A1* | 1/2016 | Yuan | G05F 1/46 323/280 |
| 2016/0126845 A1* | 5/2016 | Cohen | H02M 3/33507 363/21.01 |
| 2016/0136426 A1* | 5/2016 | Tourrel | A61N 1/37217 607/57 |
| 2016/0336871 A1* | 11/2016 | Aungurencei | H02M 7/217 |
| 2017/0126021 A1* | 5/2017 | Desrosiers | H02J 7/00308 |
| 2017/0189699 A1* | 7/2017 | Dellamano | H02J 7/00 |
| 2017/0250575 A1 | 8/2017 | Wong et al. | |
| 2018/0199854 A1* | 7/2018 | Forsell | H04B 13/005 |
| 2019/0356151 A1* | 11/2019 | Wu | H02J 50/05 |
| 2020/0076320 A1* | 3/2020 | Schuster | H02M 1/08 |
| 2020/0144927 A1* | 5/2020 | Le | H02M 1/143 |
| 2020/0195164 A1* | 6/2020 | Zhan | H02M 7/219 |
| 2020/0244176 A1* | 7/2020 | Gao | H05B 47/10 |
| 2022/0062620 A1* | 3/2022 | Roe | H02J 50/80 |
| 2023/0040473 A1* | 2/2023 | Gu | H02J 50/12 |

\* cited by examiner

RECTIFIER AND THE TIMING OF SWITCHING OF CAPACITORS

CROSS-REFERENCE TO RELATED APPLICATION

This application claims the benefit of U.S. Application Ser. No. 63/072,440, filed Aug. 31, 2020.

FIELD

The present technology is generally related to implantable medical devices such as a left ventricular assist device (LVAD), and more particularly to an internal coil interface within an implanted medical device for the timing of switching of capacitors to modulate a signal applied to the internal coil of a transcutaneous energy transfer system (TETS).

BACKGROUND

Referring to FIG. 1, an implantable LVAD system 10 has internal components (in the body of the patient) and external components. The LVAD system 10 may typically include an LVAD pump 12 an implanted controller (i-controller) 14 having an internal battery 16, an implanted internal transcutaneous energy transfer system (TETS) coil (i-coil) 18, an external TETS coil (e-coil) 20 and an external power transmitter 21 with a detachable battery 24. In operation, power is supplied from the external power transmitter 21 to the i-controller 14 via mutual coupling of the coils 18 and 20, in order to charge the internal battery 16 of the i-controller 14 and to power the LVAD pump 12. The coils 18 and 20 transfer power by mutual induction of electromagnetic energy over the air and through the body. The power supplied by the external power transmitter 21 may come from the detachable battery 24 or from a wall outlet, for example.

SUMMARY

The techniques of this disclosure generally relate to a rectifier within an implanted medical device and the timing of switching of capacitors within the implanted medical device.

According to one aspect, the present disclosure provides an internal coil interface implantable within the body of a patient as part of a left ventricular assist device (LVAD) system or other implanted medical device system. The internal coil interface is configured to provide voltage rectification of a time-varying periodic signal received on the internal coil, the internal coil interface includes: an active rectifier circuit configured to switch rectifier states to rectify the signal received from the internal coil, the switching being synchronized with an enable signal. The internal coil interface also includes a first comparator to determine when the received voltage falls below a first threshold and to determine when the received voltage rises above the first threshold and a second comparator to determine when the received voltage falls below a second threshold lower than the first threshold and to determine when the received voltage rises above the second threshold. The internal coil interface includes a digital timing circuit configured to initiate a sequence for starting a time window each time the received voltage falls below the first threshold. The digital timing circuit is further configured to generate the enable signal, the enable signal transitioning between enable states in response to the received voltage crossing the second threshold. Each time window ends in response to a transition between enable states of the enable signal after the start of the time window. A duration of a time window is dependent upon a load of internal circuitry of the implanted medical device. The internal coil interface also includes switching circuitry to connect the load to the rectified received voltage during a first time window and to disconnect the load from the rectified received voltage during a second time window.

According to this aspect, in some embodiments, the received voltage equals a voltage across internal circuitry of the medical device during the first and second time windows. In some embodiments, the first and second time windows are of unequal duration. In some embodiments, the first window is subsequent to the second window. In some embodiments, the load includes a load configured to be modulated to encode information concerning internal circuitry of the medical device. In some embodiments, modulation of the load affects a duration of a time window. In some embodiments, a change in the load affects a duration of a time window. In some embodiments, the duration of a time window increases when the load increases and the duration of the time window decreases when the load decreases. In some embodiments, the active rectifier circuit delays switching rectifier states after the received voltage falls below the first threshold for a period of time, the period of time being dependent upon a duration of time the received voltage falls below the second threshold. In some embodiments, the delay in switching rectifier states increases when the rectifier switches state before the received voltage falls below the second threshold and the delay in switching rectifier states decreases when the rectifier switches states for an interval of time after the received voltage falls below the second threshold.

According to another embodiment, an internal coil interface for a medical device having an internal coil and internal circuitry is provided. The internal coil interface includes a first comparator configured to determine when a time-vary periodic voltage received from the internal coil falls crosses a first threshold and a second comparator configured to determine when the received voltage falls crosses a second threshold lower than the first threshold. The internal coil interface includes a rectifier configured to rectify the voltage received from the internal coil, the rectifier switching between rectifier states in response to an enable signal. The internal coil interface further includes digital timing circuitry configured to: estimate a first window of time for which the received voltage equals a voltage across the internal circuitry, the estimate being based at least in part on when the received voltage crosses the first threshold; and generate the enable signal for causing the rectifier to switch between rectifier states based at least in part on when the received voltage falls below the second threshold. The internal coil interface also includes switching circuitry configured to connect a load to the rectified received voltage during the estimated first window of time.

According to this aspect, in some embodiments, the load is a load configured to be modulated to encode information concerning the internal circuitry to enable closed loop power regulation. In some embodiments, a duration of the estimated first window in time is based at least in part on modulation of the load. In some embodiments, the digital timing circuitry is further configured to estimate a second window of time for which the received voltage equals the voltage across the internal circuitry, and the switching circuitry is further configured to disconnect a load to the rectified received voltage during the estimated second window of time for which the received voltage equals the voltage across the internal circuitry. In some embodiments, the rectifier is configured to delay switching rectifier states for a first time interval in response to the received voltage falling below the first threshold. In some embodiments, when the delay causes the rectifier to switch rectifier states after the received voltage falls below the second threshold, the delay is decreased. In some embodiments, when the delay causes the rectifier to switch rectifier states before the received voltage falls below the second threshold, the delay is increased. In some embodiments, when the received voltage equals the voltage across the internal circuitry, power from the internal coil is transmitted to the internal circuitry. In some embodiments, when the received voltage does not equal the voltage across the internal circuitry, current from the internal coil is delivered to a tuning capacitor. In some embodiments, a change in the load affects a duration of the estimated first window of time. In some embodiments, the switching circuitry comprises NMOS type transistors. In some embodiments, the load is a capacitance. In some embodiments, the estimate of the first window of time is based at least in part on whether a previous estimate of a time at which the received voltage will cross the first threshold is earlier or later than a time at which the crossing of the first threshold by the received voltage actually occurred.

According to yet another aspect, an internal coil interface for an implanted medical device having an internal coil and internal circuitry is provided. The internal coil interface includes a memory configured to store timing information about when an internal coil voltage crosses voltage thresholds, the voltage threshold crossings defining successive windows. The memory is also configured to store timing information about when a capacitance is switched into and out of a load modulation circuit that modulates a load on the internal coil during each window. The timing information of an nth window of N successive windows after the capacitance is switched into or out of the load modulation circuit at a first switching time is associated with the timing information of an nth window of N windows following each of M times that the capacitance is once again switched into or out of the load modulation circuit to form a collection of M+1 sets of N windows, where n, N and M are each integers greater than zero. The internal coil interface also includes processing circuitry configured to: for each nth window in the collection of M+1 of the nth windows, predict a first predicted time of a first voltage level crossing of the internal coil voltage in the nth window after the capacitance is switched into or out of the load modulation circuit for the (M+1)th time. When a time of switching the capacitance precedes the predicted time of the first voltage level crossing, then the internal coil interface predicts that a voltage level crossing in an nth window after a next subsequent switching of the capacitance will occur earlier than the predicted time. When a time of switching the capacitance follows the predicted time of the first voltage level crossing, then the internal coil interface predicts that a voltage level crossing of an nth window after a next subsequent switching of the capacitance will occur later than the predicted time.

According to another aspect, a method of timing the switching of a capacitance into or out of a modulated load circuit in an internal coil interface of an implanted medical device, the modulated load circuit being modulated by the switching in order to communicate information from the implanted medical device to an external device via mutual coupling between an internal coil and an external coil, is provided. The method includes predicting a time of a first voltage level crossing by a voltage at a terminal of the internal coil for each of a plurality of successive windows each time the capacitance is switched into the modulated load circuit or each time the capacitance is switched out of the modulated load circuit. The method further includes adjusting the predictions based on whether a previous prediction of a time of a first voltage level crossing for a window was later or earlier than a time at which the first voltage level crossing actually occurred. In some embodiments, the digital timing circuitry is further configured to estimate successive windows of time for which the received voltage equals a voltage across the internal circuitry in response to a system perturbation.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

Figure 1:
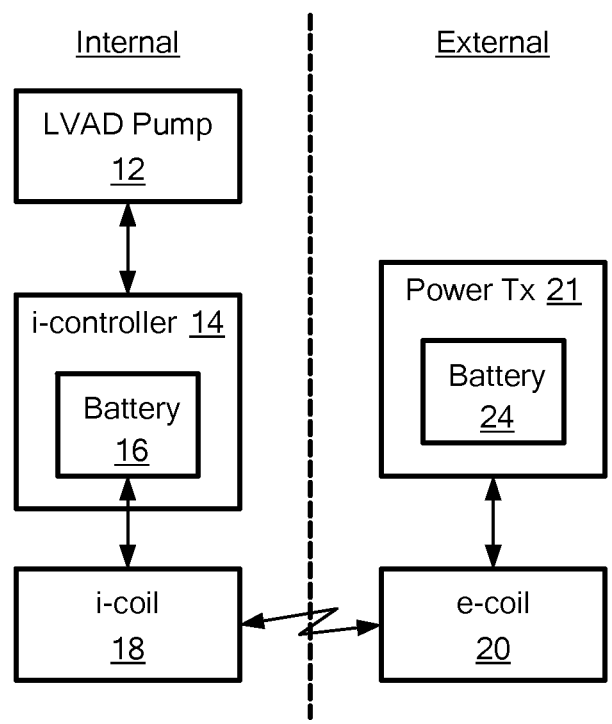
FIG. 1 is a block diagram of an implantable medical device.
Figure 2:
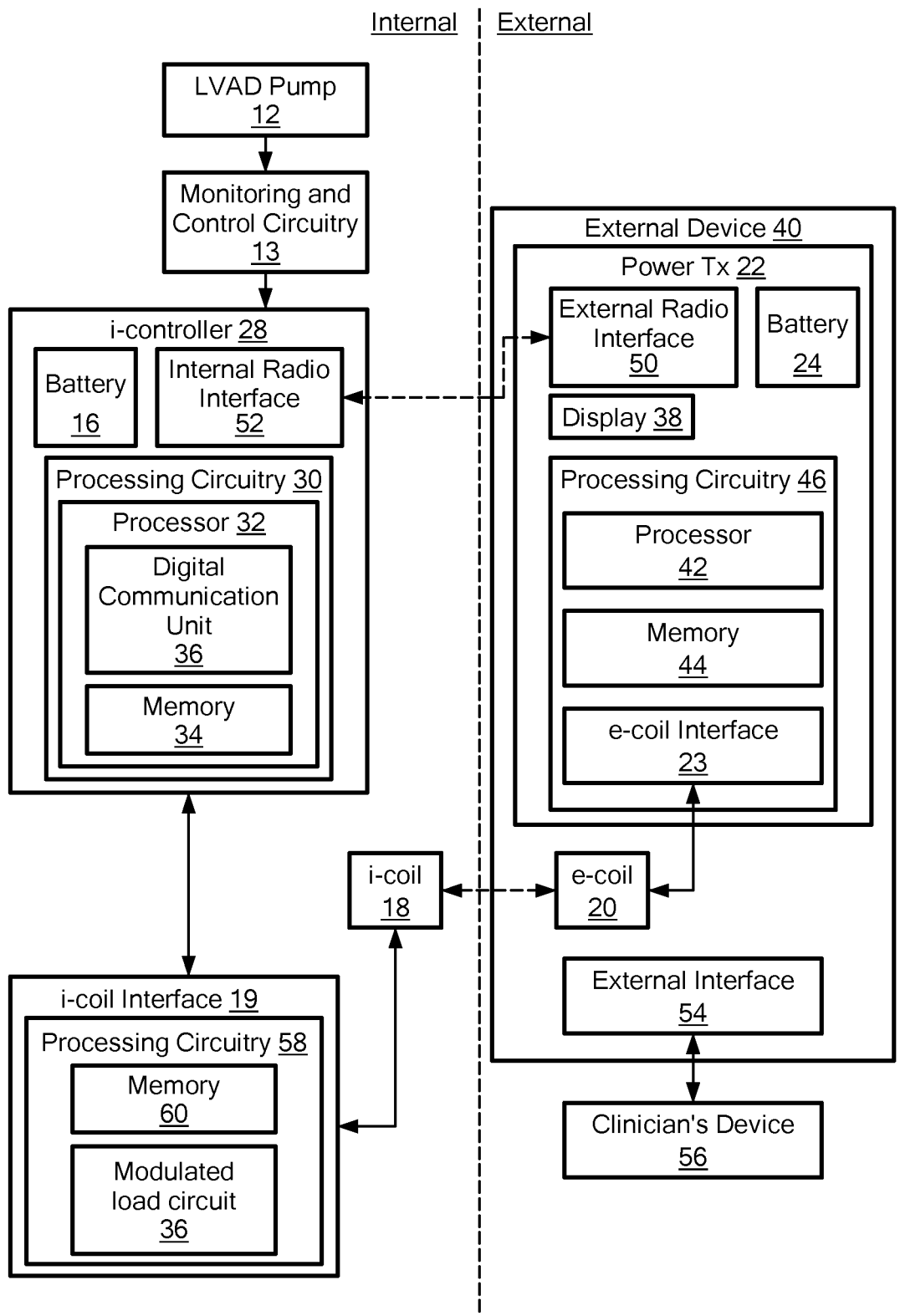
FIG. 2 is a block diagram of an embodiment of an LVAD system that implements a process of timing the switching of capacitors within an implanted medical device.

Some embodiments described herein are related to an internal coil interface within an implanted medical device for the timing of switching of capacitors to modulate a signal applied to the internal coil. Referring again to the drawing figures, FIG. 2 is a block diagram of one example configuration of an implanted medical device system 26 having external components such as a power transmitter 22, and internal components such as an internal controller (i-controller) 28 configured to perform functions described herein. As used herein, the term "implanted medical device system 26" refers to the system that includes both the implanted/implantable components as well as external components described herein.

The i-controller 28 may have processing circuitry 30 which may include a processor 32 and an internal memory 34. The processor 32 may be configured to execute computer instructions stored in the internal memory 34. Those instructions may include instructions to cause the processor to perform some of the processes described in more detail below. The processor 32 may therefore implement a digital communication circuit 36, which is described with reference to FIG. 4.

A message or result from the digital communication unit 36 may be transferred from the i-controller 28 to an external display 38 of an external device 40, which may include a processor 42 and a memory 44 within processing circuitry 46, the external power transmitter 22 and the detachable battery 24, as well as the e-coil 20 in some embodiments. The memory 44 may be configured to store computer instructions to be executed by the processor 42. The external display 38 may be configured to display information received from the i-controller 28.

Electrical communication of signals and power between the internal components of i-controller 28 may be via communication busses and individual electrical conductors not shown in FIG. 2. For example, a multi-conductor address bus and data bus may connect processor 32 with internal memory 34. In some embodiments, an i-coil interface 19 associated with i-coil 18 may be included in the set of internal components making up the implanted medical device system 26. One purpose of i-coil interface 19 may be to modulate the alternating current applied to the i-coil 18 with signals from the i-controller 28 to be transmitted from the i-coil 18 to the e-coil 20 and/or to demodulate signals to be received by the i-coil 18 from the e-coil 20. In some embodiments, a purpose of the i-coil interface 19 is to provide conversion between the alternating current (AC) of the i-coil 18 and direct current (DC) to charge the battery 16.

The i-coil interface 19 may include processing circuitry 58 which includes a memory 60 to perform the functions and procedures for timing the switching of capacitances into and out of a modulated load circuit 61. The modulated load circuit 61 includes the capacitances which, when switched into or out of the modulated load circuit 61, modulate a signal applied to the internal coil which is inductively communicated to the power transmitter 22 via the e-coil 20. The modulation causes the applied signal to carry information that is generated and/or formatted and/or encoded by the digital communication unit 36.

The power supplied to the i-coil 18 may be adjusted by varying the AC electrical current in the e-coil 20. Some or all functions of the i-coil interface 19 may be included in the i-controller 28 and/or the i-coil 18. In some embodiments, the i-coil 18 and/or i-coil interface 19 may be internal to or considered part of the internal controller 28. Similarly, electrical communication of signals and power between the internal components of external device may be by communication busses and individual electrical conductors not shown in FIG. 2. For example, a multi-conductor address bus and data bus may connect processor 42 with memory 44. In some embodiments, an e-coil interface 23 associated with e-coil 20 may be included in the set of external components making up the implanted medical device system 26. The e-coil interface 23 may include a TETS interface configured to demodulate information signals from the processing circuitry 30 transmitted from the i-coil 18 to the e-coil 20. The e-coil interface 23 may also be configured to couple power from the external power transmitter 22 to the e-coil 20. In some embodiments, the e-coil interface 23 may be two distinct units, one unit for demodulation of signals from the i-controller that are uploaded via the coils 18 and 20, and one unit for coupling power from the external power transmitter 22 to the e-coil 20. In some embodiments, the i-controller 28 may upload information to the power transmitter 22 via the coils 18 and 20, but the power transmitter does not download information to the i-controller 28 via the coils 18 and 20.

In some embodiments, the internal components of the implanted medical device system 26 may include monitoring and control circuitry 13. A purpose of monitoring and control circuitry 13 may include monitoring speed and temperature, for example, of the LVAD pump 12. Another purpose of the monitoring and control circuitry 13 may include controlling the speed of the LVAD pump 12. Another purpose of the monitoring and control circuitry 13 may include monitoring the temperature of the i-controller 28, the i-coil 18 and/or the implanted battery 16. In some embodiments, some or all of the monitoring and control circuitry 13 may be incorporated into the LVAD pump 12 and/or the i-controller 28. In some embodiments, some or all of the functions performed by the monitoring and control circuitry 13 may be performed by the processing circuitry 30. Thus, in some embodiments, the monitoring and control circuitry 13 may include one or more temperature sensors embedded in the LVAD pump 12, the i-controller 28, the i-coil 18 and/or implanted battery 16. Information obtained from and/or about the LVAD pump 12, such as speed and temperature, may be sent to the external device 40 to be displayed by external display 38.

The various internal components making up the LVAD system may be grouped into one or more separate housings. Similarly, the various external components making up the LVAD system may be grouped into one or more separate housings. Further, some of the components shown and described as being internal to the i-controller 28 may be instead, external to i-controller 28 in some embodiments. Similarly, some of the components shown and described as being internal to the external device 40 may be instead, external to external device 40, in some embodiments. Note further that some of the functions performed by processor 32 may be performed instead by processor 42.

Note that transfer of information from the external device 40 to the internal memory 34, and vice versa, may be by wireless radio frequency (RF) transmission (over the air and through the body when the i-controller 28 is implanted). Accordingly, in some embodiments, the external device 40 includes an external radio interface 50 and the i-controller 28 includes an internal radio interface 52. In some embodiments, the external radio interface 50 and the internal radio interface 52 are RF transceivers having both an RF receiver for receiving information wirelessly and an RF transmitter for transmitting information wirelessly. Such RF transceivers may be Bluetooth and/or Wi-Fi compliant, for example. In some embodiments, the RF receiver and RF transmitter within the external device 40 or within the i-controller 28 are integrated into one unit, whereas in some embodiments, they could be physically separate units.

Also, information may be communicated to the i-controller 28 from the power transmitter 22 via the coils 18 and 20, by modulating a parameter of power transmission, such as modulating the frequency of the transmitted power, or by modulating a parameter of the i-coil interface 19, for example, by modulating a tuning capacitance of the i-coil interface 19 or by modulating the load level of the i-controller and/or the i-coil interface 19.

The external device 40 could be a patient's external device that has an external interface 54 which provides an interface between the external device 40 and a clinician's device 56. The clinician's device might, for example, have a Universal Serial Bus (USB) port and interface 54 might include a USB port, so that a USB cable may connect the two ports. The clinician's device 56 may read data from the external device 40 and write information and control signaling to the external device 40, in some embodiments. In the alternative to a wireline connection, the interface 54 could include or be a radio interface.

Figure 3:
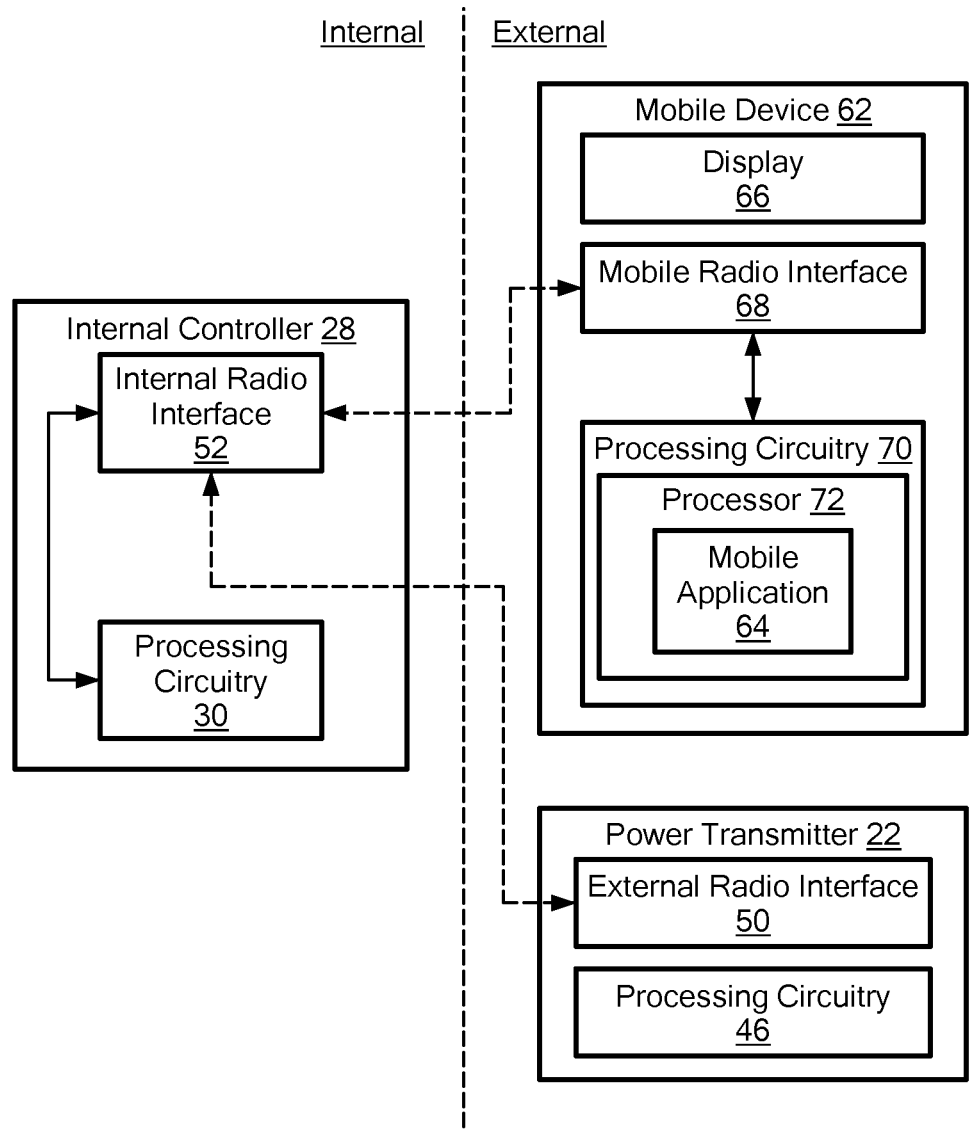
FIG. 3 is a block diagram of an embodiment that includes a mobile device.

FIG. 3 is a block diagram of an implanted medical device system 26 that includes a mobile device 62 with a mobile application 64 in wireless communication with the i-controller 28. The mobile device 62 may be a mobile phone or other mobile digital device that can process information and communicate wirelessly with the i-controller. Accordingly, the mobile device 62 has a display 66, a mobile radio interface 68, processing circuitry 70 and a processor 72 which runs the mobile application 64. The radio interfaces 50, 52 and 68 may be Bluetooth Low Energy compatible radio interfaces, and the i-controller 28 may be a peripheral device responsible for advertising, while the mobile device 62 and the external power transmitter 22 may operate as master or central devices responsible for scanning and issuing connection requests.

Communication from the i-controller 28 to the external power transmitter 22 enables display on display 38 of implanted device information such as pump data and alarm indications. The i-controller 28 may exchange, via the radio interfaces 50 and 52, diagnostic and log file data with the external power transmitter 22. The i-controller 28 may receive programming commands from an external device such as the clinician's device 56 or mobile device 62. Further, communication from the i-controller 28 to the mobile device 62, via the radio interfaces 52 and 68, enables remote monitoring in cases where the mobile device 28 is connected to the Internet, and enables the display 66 to display information about the state of the implanted portion of the implanted medical device system 26 such as, for example, remaining battery runtime. In some embodiments, the internal radio interface 52 may only communicate with the external radio interface 50 and the mobile radio interface 68 one at a time. In some embodiments, when the i-controller 28 is not engaged in a communication session with an external device, such as external power transmitter 22 or mobile device 62, the i-controller 28 may advertise continually to enable rapid reestablishment of the wireless connection between the i-controller 28 and the external power transmitter 22 or mobile device 62. Conversely, either one or both of the external power transmitter 22 or mobile device 62 may scan for such advertisements.

Figure 4:
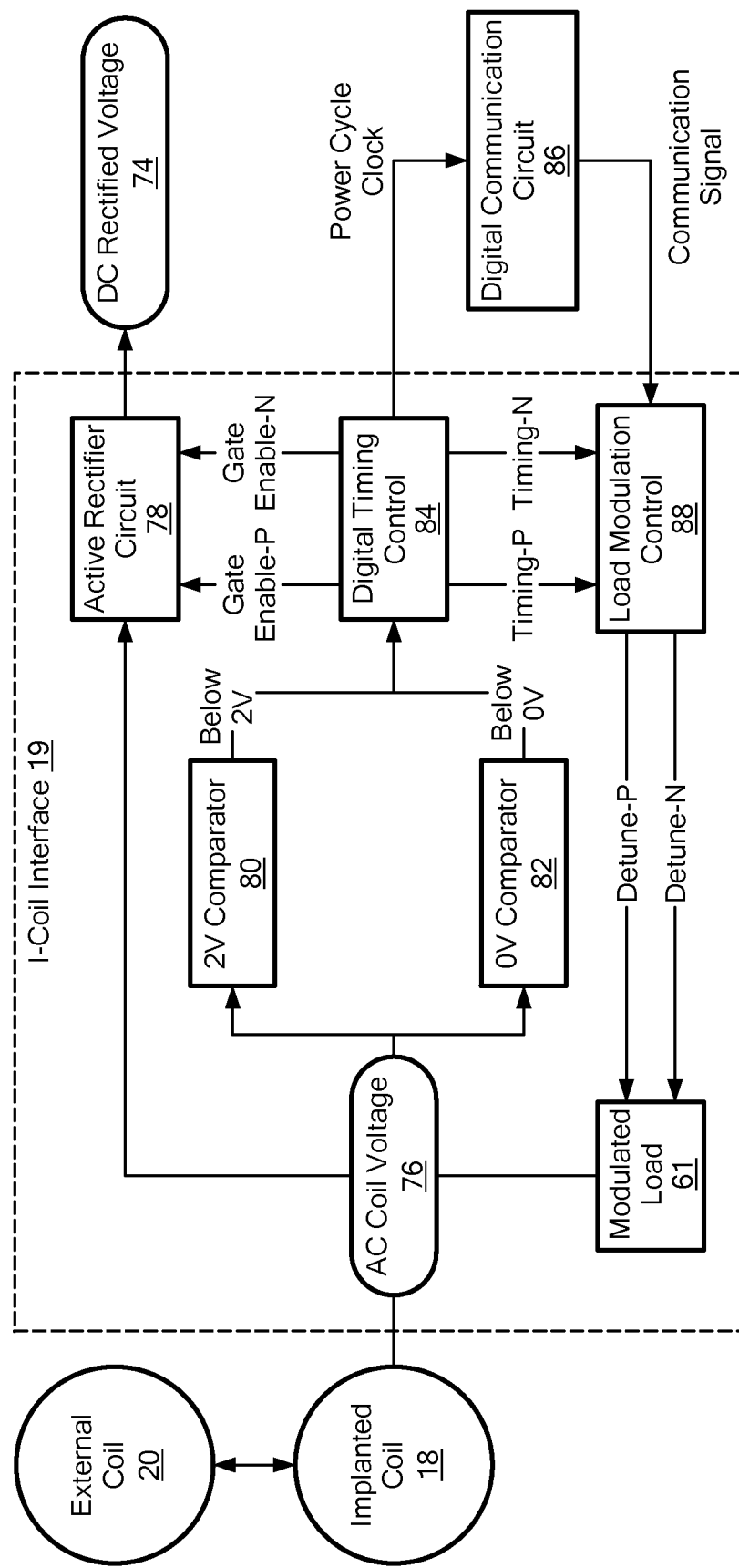
FIG. 4 is a block diagram of an internal coil interface configured according to principles set forth herein.

FIG. 4 is a block diagram of circuitry configured to provide a DC rectified voltage 74 which is generated from a power signal inductively transmitted from the e-coil 20 to the i-coil 18. This induces in the i-coil 18 an AC coil voltage 76. The AC coil voltage 76 is received by the active rectifier circuit 78, which rectifies the AC coil voltage 76 to produce the DC rectified voltage 74. The AC coil voltage 76 is also sent to a first voltage comparator 80 and a second voltage comparator 82. The first voltage comparator 80 compares the AC coil voltage 76 to a first threshold to produce a first compare signal. The second voltage comparator 82 compares the AC coil voltage 76 to a second threshold lower than the first threshold to produce a second compare signal. For example, the first threshold may be 2 volts and the second threshold may be 0 volts. In some embodiments, the first and second thresholds are fixed and do not change over time. The first and second thresholds may be determined based on characteristics of transistor circuits included in the active rectifier circuit 78.

In the example of FIG. 4, when the AC coil voltage 76 falls below 2 volts, a signal indicating this fact is sent from the first voltage comparator 80 to a digital timing control circuit 84. The two volt reference signal may be in reference to the ground of the i-controller 28. Also, rectifier circuitry 78 holds a higher potential signal in the i-coil 18 to the positive supply voltage of the i-controller 28. Similarly, when the AC voltage falls below 0 volts, a signal indicating this fact is sent from the second voltage comparator 82 to the digital timing control circuit 84. The signals enable the digital timing control circuit 84 to generate a gate enable-P signal and a gate enable-N signal. The gate enable-P signal and the gate enable-N signal control rectification of the AC coil voltage 76 by the active rectifier circuit 78. The digital timing control circuit 84 may also generate a power cycle clock to control timing of a digital communication circuit 86. The digital communication circuit 86 generates communication signals to a load modulation control circuit 88. The communication signals sent to the load modulation control circuit 88 may include information to be transmitted from the i-controller 28 to the power transmitter 22 via the i-coil 18 and the e-coil 20. The load modulation control circuit 88 generates two load modulation signals: a detune-P enable signal and a detune-N enable signal. These signals are used to modulate a load of the modulated load circuit 61. Modulation of the modulated load circuit 61 causes the AC coil voltage 72 to vary.

In some embodiments, the components numbered 74 through 84, 88 and 61 may be implemented within the i-coil interface 19 and/or the i-controller 28. The digital communication circuit 86 may be implemented within the i-controller 28 as digital communication unit 36.

A purpose of the i-coil interface 19 is to determine the appropriate timing for connecting the i-coil 18 to the load presented by the implanted circuitry in order to pass energy to such load. The appropriate time to make this connection is when the voltage on the i-coil 18 is equal to the voltage on the implanted circuitry, including the i-controller 28. This timing is not directly measured, but rather is estimated. The signal from the first voltage comparator 80 signals when the AC coil voltage 76 is approaching the second threshold.

Figure 5:
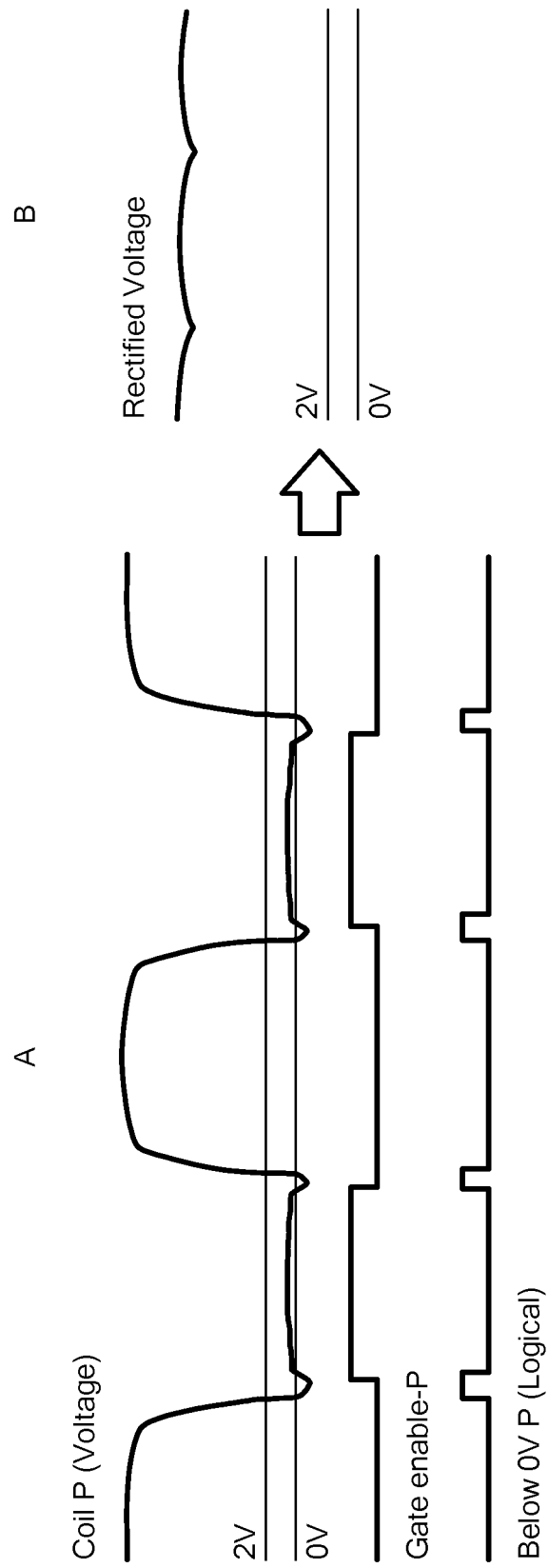
FIG. 5 is a timing diagram showing timing of the voltage on a coil terminal, examples of thresholds, and an enable signal.

FIG. 5 is a timing diagram that shows the timing relationships between the AC coil voltage 76 and the gate enable-P signal. For the example of FIG. 5, the first threshold is 2 volts and the second threshold is zero volts. The signal at the top of side A of FIG. 5 is the AC coil voltage on a P terminal of the i-coil 18. In a first cycle, the AC coil voltage on the P terminal of the i-coil 18 falls below the 2 volt threshold and then falls below the 0 volt threshold for a short period of time, resulting in the below 0V logic signal at the bottom of side A of FIG. 5. In the timing example of FIG. 5, at about the time that the AC coil voltage on the P-terminal of the i-coil 18 crosses the 0 volt threshold, the gate enable-P signal shown on side A of FIG. 5, transitions from low to high. Note that a similar timing relationship may exist for the AC coil voltage on the N terminal of the i-coil 18. The P terminal AC coil voltage may be 180 degrees out of phase with the N terminal AC coil voltage. Similarly, the gate enable-P signal may be 180 degrees out of phase with the gate enable-N signal. Side B of FIG. 5 shows the DC rectified voltage 74 desirably having ripple that is smaller than a maximum tolerable ripple.

Figure 6:
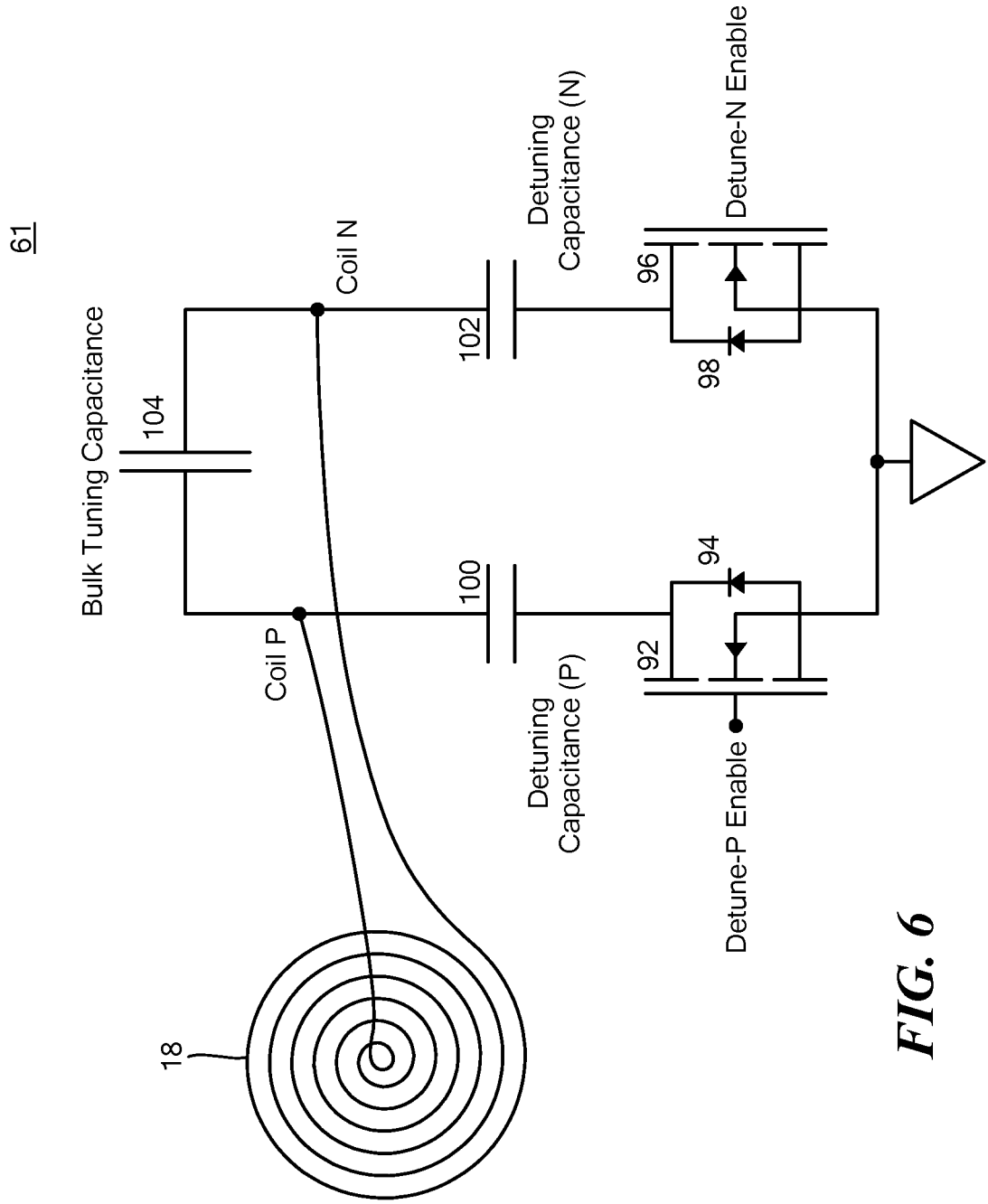
FIG. 6 is schematic of a modulated load circuit responsive to enable signals.

FIG. 6 illustrates the i-coil 18 in electrical communication with an example of the modulated load circuit 61. One terminal of the i-coil 18 is electrically connected as shown in FIG. 6 to a P-side of the modulated load circuit 61 and another terminal of the i-coil 18 is electrically connected to an N-side of the modulated load circuit 61. The P-side of the modulated load circuit 61 has a first transistor 92 and a first diode 94. The N-side of the modulated load circuit 61 has a second transistor 96 and a second diode 98. The first transistor 92 receives the detune-P enable signal from the load modulation control circuit 88 and the second transistor 96 receives the detune-N enable signal from the load modulation control circuit 88. The P-side of the modulated load circuit 61 and the N-side of the modulated load circuit 61 also include first detuning capacitance 100 and second detuning capacitance 102, respectively. The modulated load circuit 61 may also include a bulk tuning capacitance 104 that is series with the two detuning capacitances 100 and 102. By modulating the capacitance connected to the i-coil 18, a modulated signal is developed on the e-coil 20. The modulation is according to the communication signal received by the load modulation control circuit 88 from the digital communication circuit 86. The modulated signal on the e-coil may be decoded by the processing circuitry 46 of the power transmitter 22 to determine the information encoded by the modulation. Note that in some embodiments, first transistor 92 and second transistor 96 have an NMOS transistor topology, while in some other embodiments, first transistor 92 and second transistor 96 have an NPN bipolar transistor topology.

The first and second detuning capacitances 100 and 102 may be switched into and out of the circuit shown FIG. 6. The detune-P and detune-N enable signals determine when within a power cycle the detuning capacitances 100 and 102 can be switched. Whether the capacitors actually are switched is determined by what specific data bits are being transmitted.

In some embodiments, the data bits are phase shift keyed where each encoded data bit consists of at least one transition of the capacitor connection, with the timing of transitions determined by whether the data bit is a data0 or data1 bit. In some embodiments the data bits are on-off keyed where the capacitor connection is switched in or out depending on whether the data bit is a data0 or data1 bit. In some embodiments, frequency keying may be employed, where the capacitor connection is performed at a faster or slower rate depending upon the data bit being data0 or data1. Multibit symbols are also possible, for example, as opposed to a phase shift of 180 degrees for data1 and 0 degrees for data0, a phase shift of 0 degrees could represent data00, 90 degrees for data01, 180 degrees for data11 and 270 degrees for data10.

As noted above, the time for switching a capacitor into or out of to make this connection is when the voltage on the i-coil 18 is equal to the voltage on the implanted circuitry. In some embodiments, when the first detuning capacitance 100 is switched into the circuit the second detuning capacitance 102 is switched out of the circuit, and vice versa. The timing of when these switches occur is determined by the transitions of the detune enable signals from the load modulation control circuit 88. The period during which a gate enable signal is logically high may define a time window during which a corresponding detuning capacitor 100, 102 can be switched.

In the absence of any perturbations of the implanted medical device system 26, these windows retain consistent timing and change only with the slowly changing global conditions. Such global conditions may include, for example, change in the peak power level being transmitted or consumed, changes in coil-to-coil coupling, and transmit and receive voltage levels in the coils 18 and/or 20. However, the connection or disconnection, hereafter referred to as switching, of the detuning capacitances for communication of information back to the power transmitter causes a perturbation of the implanted medical device system 26. This perturbation changes the duration of the timing window for the capacitances 100 and 102 to be switched in or out of the circuit. But, since the switching is repetitive (as driven by the communication signal from the digital communication circuit 86) and the perturbations are consistent (as long as the switching occurs during the time window defined by the gate enable signals), the system can account for the perturbation by tracking the duration of the windows over successive alternate half cycles (or power pulses) of the of the AC coil voltage separately from the steady state windows (when there are no perturbations).

Tracking the duration of the windows over the successive alternate half cycles may include recording a duration and a start and stop time (hereafter referred to as window parameters) for each of a plurality of successive windows. These window parameters may be stored in a memory that is within or outside of the i-controller 28 or the i-coil interface 19. Note that some of the functions of the i-coil interface 19 may be implemented as application specific circuitry and/or processing circuitry that includes a processor and a memory. Such memory may be configured to contain multiple addressable registers (memory locations) to store the window parameters for each of plurality of successive windows with respect to when the most recently switched detuning capacitances 100, 102 were switched. As will be explained below, these window parameters are used to predict or anticipate the times of the voltage threshold crossings by the AC coil voltage 76. The start and stop times of the successive windows are determined by the voltage threshold crossings by the AC coil voltage 76, but the implanted medical device system 26 anticipates these voltage crossings based on whether a previous used time of switching a detuning capacitance 100, 102 into or out of the circuit was earlier than, later than, or coinciding with start and stop times of the corresponding window defined by voltage crossings. This anticipating involves comparing a start time of a window defined by the voltage crossings with a switching time at which a capacitance 100, 102 is switched into or out of the modulated load circuit 61.

As an example, a first window after switching a detuning capacitance 100, 102 into the modulated load circuit 61 may be shorter in duration and start significantly later than other windows. For each successive power pulse after the detuning capacitance 100, 102 is switched into the modulated load circuit 61, the duration of the window becomes longer in duration and begins earlier until the transient effects are complete (die out) and the successive windows become consistent in timing and duration. Similarly, the first window after switching a capacitance 100, 102 out of the modulated load circuit 61, may be significantly be longer in duration and start earlier, with each successive window becoming shorter in duration and starting later until the transient effects are again complete (have died out).

Figure 7:
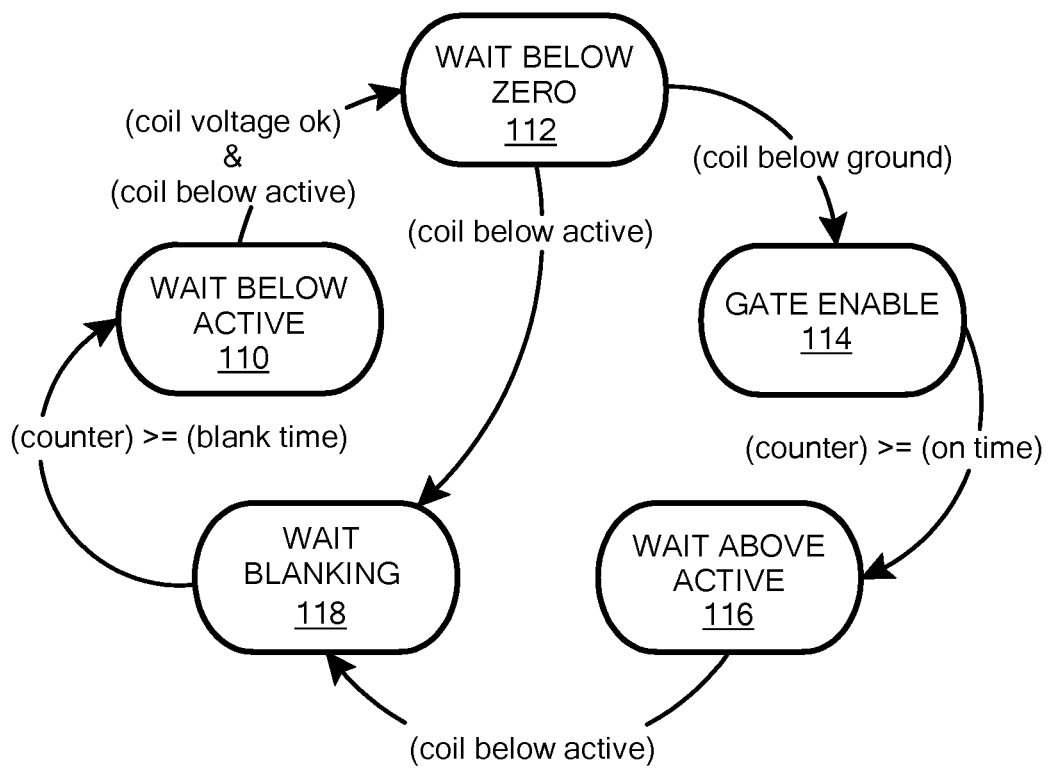
FIG. 7 is an illustration of a state diagram depicting states of an active rectifier circuit according to principles set forth herein.
Figure 8:
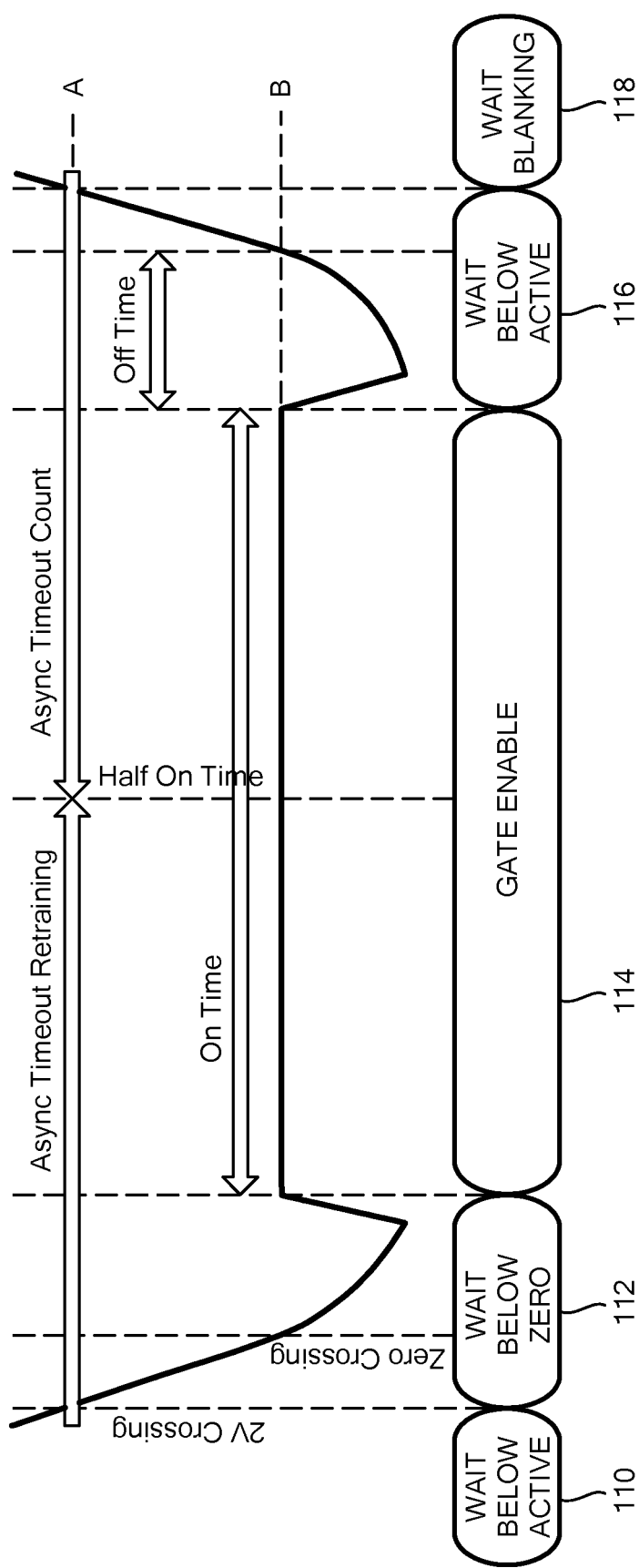
FIG. 8 is a timing diagram showing voltage level crossings and state transitions.
Figure 9:
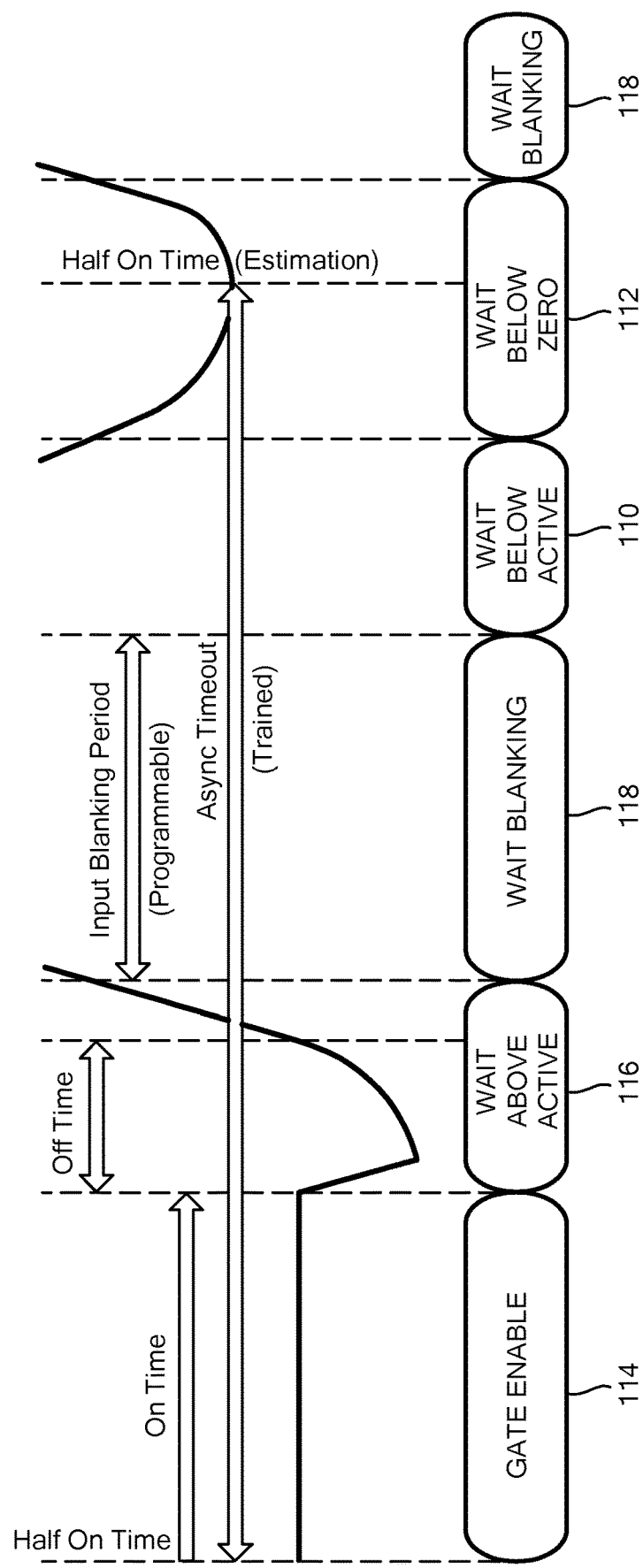
FIG. 9 is a timing diagram showing further timing transitions according to principles set forth herein.

FIG. 7 is a state diagram that illustrates the states of the active rectifier circuit 78 in some embodiments. The active rectifier circuit 78 receives two signals to control rectification timing: a 2 volt crossing signal and a zero crossing signal. FIG. 8 shows timing of the states of FIG. 7 in a normal mode of operation. Assume that the active rectifier circuit 78 is in the wait below active state 110. When the AC coil voltage 76 received by the active rectifier circuit 78 falls below the 2 volt level A, the active rectifier moves to the wait below zero state 112 during which time the AC coil voltage 76 fall below the zero volt level B and then rises to the zero volt level B. Then, the active rectifier circuit 78 enters the gate enable state 114. At the end of one half the time during which the active rectifier circuit 78 is in the gate enable state, an asynchronization timeout retraining process is performed. If a normal cycle of the AC coil voltage 76 occurs before the end of the first half of the on-time window during which the active rectifier circuit 78 is in the gate enable state 114, then the asynchronization timeout retraining process adjusts the duration of the on-time to be shorter. Here, a normal cycle refers to the AC coil voltage falling below the two volt level A and then rising above the zero volt level B. Otherwise, at the beginning of the second half of the on-time window during which the active rectifier circuit 78 is in the gate enable state 114, an asynchronization timeout count begins. In some embodiments, an on-time window is optimized or otherwise adapted to maintain a 40 Mega-Hertz (MHz) count of 2 for the off-time window. When an on-time counter rolls over, signifying the middle of the on-time window a synchronization pulse is delivered to the load modulation circuitry 88 to time the switching of the detuning capacitors 100, 102. When the AC coil voltage 76 falls below the zero volt level B, the active rectifier circuit 78 enters the wait above active state 116. During the time in the wait above active state 116, the AC coil voltage 76 rises. While the AC coil voltage 76 is below the zero volt level B, the active rectifier circuit 78 is off. When the AC coil voltage 76 crosses the 2 volt level A, the active rectifier circuit 78 enters the wait blanking state 118 and remains in the wait blanking state 118 until the expiration of a blanking period timer, as shown in FIG. 9. Upon the expiration of the blanking period timer, the active rectifier circuit 78 returns to the wait below active state 110. Suppose next that the AC coil voltage 76 falls below the 2 volt threshold and again, the active rectifier circuit 78 enters the wait below zero state 112. When an asynchronous timeout counter, which begins at the half way point of the previous on-time window, expires while the active rectifier circuit 78 is in the current wait below zero state and has not fallen below the zero volt level B, then the timing period of the asynchronization timeout counter is not adjusted. When the AC coil voltage 76 again rises above the two volt level A while the active rectifier is in the wait below zero state 112, then the active rectifier circuit 78 transitions to the wait blanking state 118.

Figure 10:
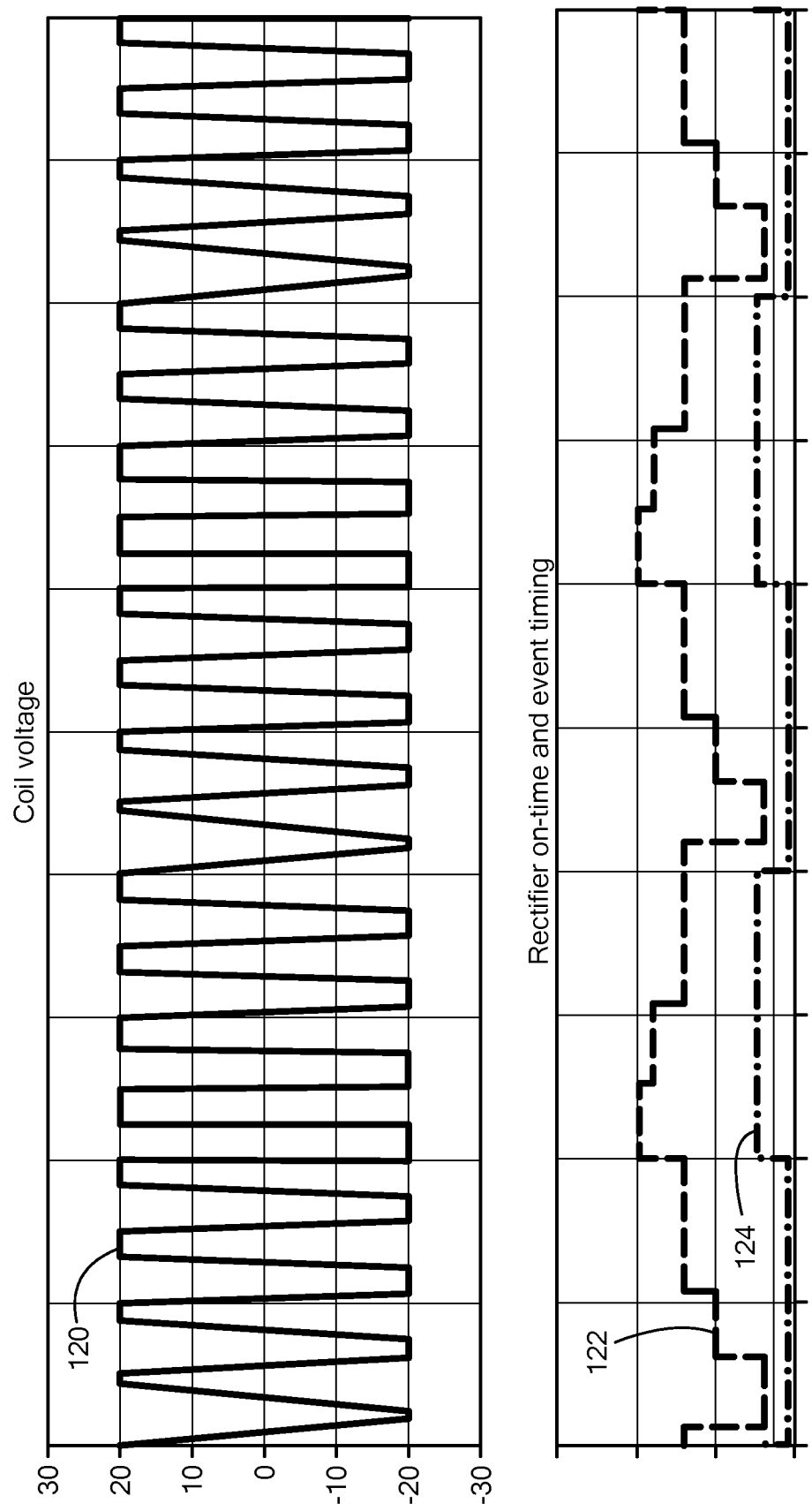
FIG. 10 is a timing diagram of an AC coil voltage and a corresponding rectifier on-time.

FIG. 10 illustrates an example AC coil voltage 120 and a corresponding graph of rectifier on-time and event timing. During the time durations when the AC coil voltage 120 is at +/−20 volts, the active rectifier circuit 78 is in an active state. The trace 122 in FIG. 10 represents the on-time of the active rectifier circuit 78. The trace 124 represent events that cause transients on the power received by the i-coil 18. Such an event may include switching load modulation capacitors in or out of the circuit. FIG. 10 is an example. In practice, more than 3 cycles may be required to reach stability. For example, it may take 8 or more cycles to reach stable operation in some embodiments. Note that operation at a stable operating point (steady state) can have a first duration, whereas operation during a transient settlement time can have a second duration.

Figure 11:
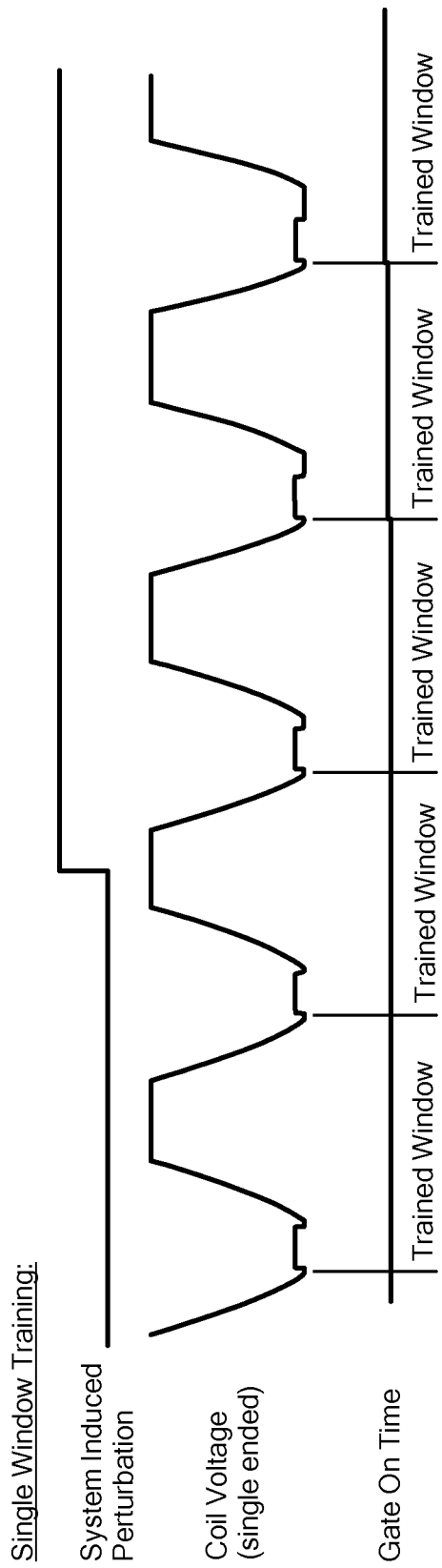
FIG. 11 is a timing diagram for training and tracking in successive windows.
Figure 12:
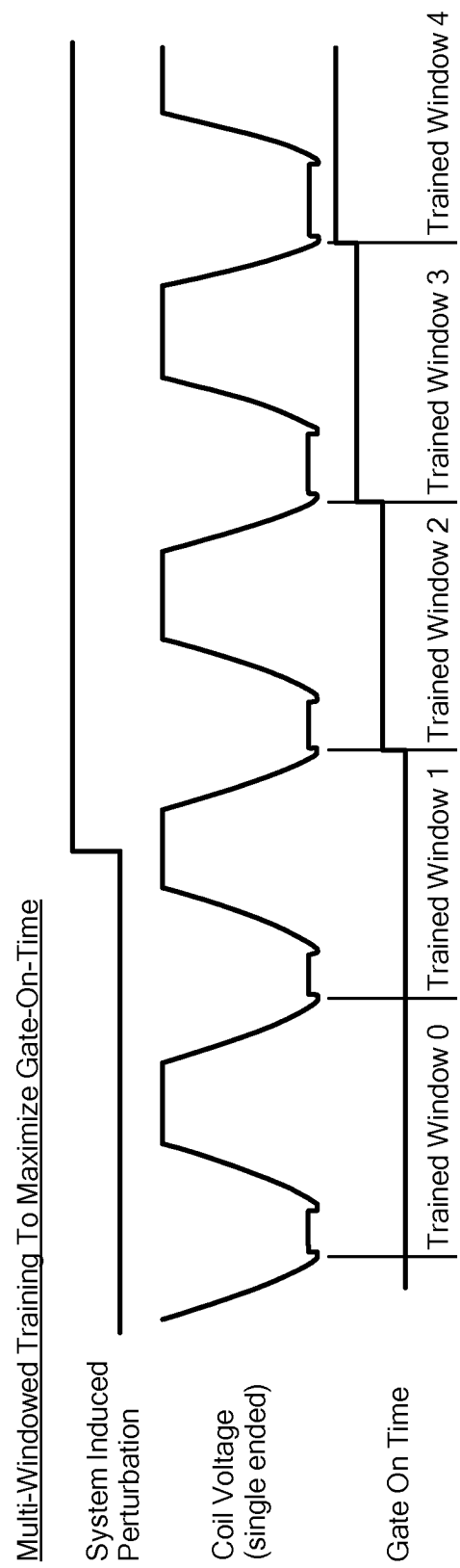
FIG. 12 is a timing diagram for training and tracking of independent successive windows.

FIG. 11 illustrates a timing diagram for training the active rectifier circuit 78 in response to a perturbation signal without separate window tracking which may, by way of example, arise from changes in the modulated load 61 induced by the digital communication circuit 86 via the load modulation control circuit 88. The AC coil voltage 120 is responsive to the gate on-time signal (gate enable-P and gate enable-N) received by the active rectifier circuit 78 from the digital timing control circuit 84. The gate on-time signal is in turn responsive to the perturbation but may not be sufficiently responsive to track the changes. Note that the timing shown in FIG. 11 is merely representative. In practice, each successive training window may differ in duration and/or the gate on-time may vary from training window to training window at a rate that is different from what is shown in FIG. 11. FIG. 12 illustrates a timing diagram that is similar to the timing diagram of FIG. 11, except that in FIG. 12, each successive training window is different. The duration of each successive training window may be the same or different. The succession of training windows is in relation to the perturbation. The training windows may be tracked and trained independently to adapt to fast changes associated with one type of perturbation, such as may be caused by the digital communication circuit 86, while also adapting to relatively slow changes, such as may be caused by changes in power level and/or coupling between the i-coil 18 and the e-coil 20.

In order for the tracking to adapt to fast changing transient conditions that occur after switching the detuning capacitors, the timing of the activation windows during which the detuning capacitors may be switched may be tracked separately based upon whether the interval is the $1^{st}$, $2^{nd}$, $3^{rd}$ or subsequent windows after the switching occurs, because the transients start out high upon switching, but die out over several subsequent successive windows. The i-coil interface 19 or i-controller 28 may also separately track the intervals during which the detuning capacitances 100 and 102 are connected and disconnected. Note that the windows during which the AC coil voltage 76 is below at least one of the first and second thresholds tend to start later and have a shorter duration when a detuning capacitance 100 or 102 is connected as compared to when the detuning capacitance 100 or 102 is disconnected. This observation may be used to better predict the timing of the voltage level crossings. Referring again to FIG. 7, the timing of window n=1, M=1, may be used to predict the timing of window n=1, M=2. Similarly, the timing of window n=2, M=1, may be used to predict the timing of window n=2, M=2, etc.

Thus, the observed time of the AC coil voltage 76 falling below a threshold may be compared to an observed time at which a capacitance 100 or 102 is switched into or out of the modulated load circuit 61 to produce a comparison signal. This comparison may be performed by one or more comparators within the i-coil interface 19 or within the processing circuitry 30 of the i-controller 28. Based on this comparison, the prediction of the time of the next voltage level crossing corresponding to the $1^{st}$, $2^{nd}$ $3^{rd}$ or subsequent windows after the switching occurs is made. For example, if a first voltage level crossing for the first window after a first capacitance switch into the circuit occurs at a first time and the predicted value of the next voltage level crossing for the first window after the next subsequent capacitance switch into the circuit turns out to have been too late, the prediction is adjusted downward, and vice versa. Adjusting the prediction downward, means predicting that the next corresponding voltage level crossing will occur earlier, relative to the next capacitance switching event.

If the predicted value turns out to be too late, the AC coil voltage 76 coil is larger than the voltage on the implanted circuitry, as energy delivered to the i-coil 18 is being conducted by the one of the diodes 94 and 98 that is forward biased. The excess voltage on the i-coil 18 is the forward bias voltage of the respective conducting diode. Digital circuitry in the digital timing control circuit 84 may set a delay timer starting at the first compare signal that is used to switch the active rectifier circuit 78. The delay timer may be configured to end based on the time of the predicted next corresponding voltage level crossing of the AC coil voltage 76. If the active rectifier circuit 78 is switched too early, the second compare signal will be absent and the digital timing control circuit 84 will increase the delay for the next time the delay timer implemented by the digital timing control circuit 84 is used. If the active rectifier circuit 78 is switched too late, the second compare signal will be present and will have an extended duration and the digital circuitry will then decrease the delay for the next time the delay timer is used. If the active rectifier circuit 78 is switched at a time that coincides with the switching of a detuning capacitance 100 or 102, the second compare signal will be present, but short.

When the active rectifier circuit 78 is switched, the i-coil 18 is connected to the implanted circuitry, which causes the voltage on the i-coil 18 and the implanted circuitry to be the same. In such case, the current in the i-coil 18 is transmitted to the implanted circuitry as received power rather than to the detuning capacitances 100, 102, to build up additional voltage on the i-coil 18.

Figure 13:
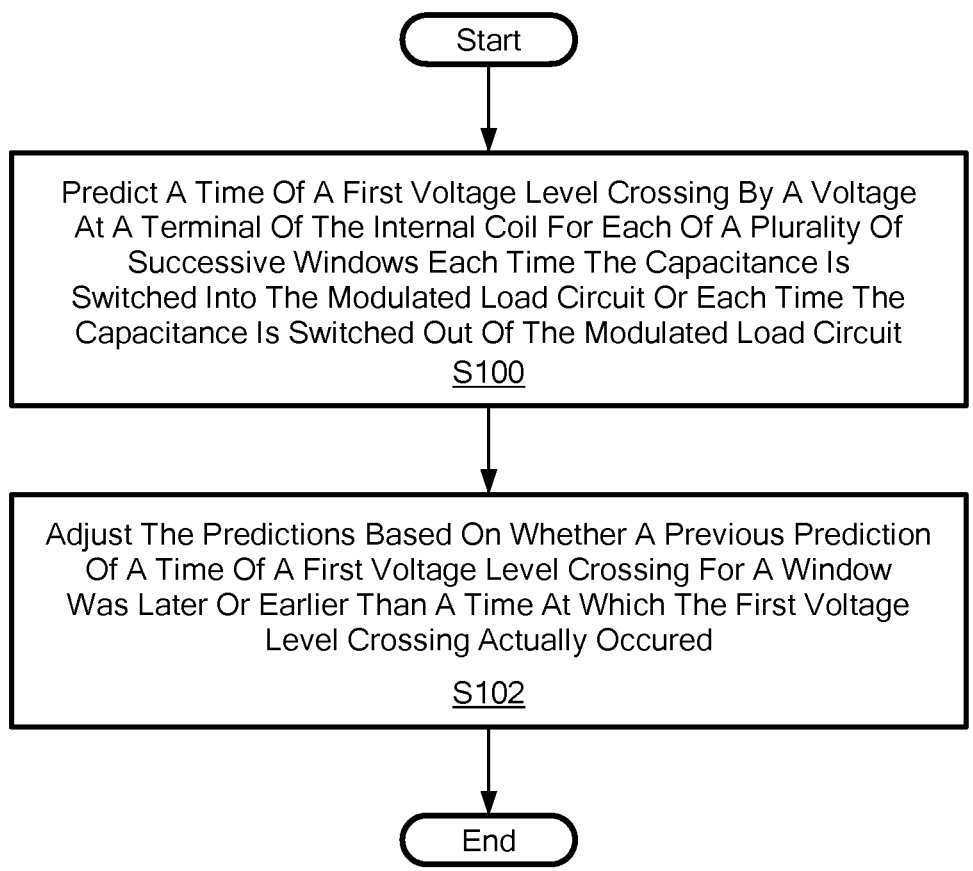
FIG. 13 is a flowchart of an example process for tracking in multiple windows.

FIG. 13 is a flowchart of an example process implemented in an internal device of an implantable medical device system 26 for timing of switching a detuning capacitance 100, 102 into or out of a modulated load circuit 61 in order to communicate information from the internal device to an external device via mutual induction between an internal coil 18 of the internal device and an external coil 20 of the external device. The process includes predicting, via the processing circuitry 58, a time of a first voltage level crossing by a voltage at a terminal of the internal coil 18 for each of a plurality of successive windows each time the detuning capacitance 100, 102 is switched into the modulated load circuit 61 or each time the detuning capacitance 100, 102 is switched out of the modulated load circuit 61 (Block S100). The process also includes adjusting, via the processing circuitry 5, the predictions based on whether a previous prediction of a time of a first voltage level crossing for a window was later or earlier than a time at which the first voltage level crossing actually occurred (Block S102).

In some embodiments an adjustment time step for the predictions may be larger in one direction than the other. For example, if the timing at the start of an interval adjusts more for early timing than for late timing, a percentage of events that are early, as opposed to late, will not be 50% but rather, will be skewed to have more late events than early events. The digital timing control circuitry 84 can also utilize the pulse width of the below 0V signal as an indication of how late the beginning timing is or how early the end timing is, and adjust the timing faster if the pulse width is wide in order to more rapidly adjust to significantly wrong timing intervals.

According to one aspect, the present disclosure provides an internal coil interface 19 implantable within the body of a patient as part of a left ventricular assist device (LVAD) system or other implanted medical device system 26. The internal coil interface 19 is configured to provide voltage rectification of a time-varying periodic signal received on the internal coil 18, the internal coil 18 interface includes: an active rectifier circuit 78 configured to switch rectifier states to rectify the signal received from the internal coil 18, the switching being synchronized with an enable signal. The internal coil interface 19 also includes a first comparator 80 to determine when the received voltage falls below a first threshold and to determine when the received voltage rises above the first threshold and a second comparator 82 to determine when the received voltage falls below a second threshold lower than the first threshold and to determine when the received voltage rises above the second threshold. The internal coil interface 19 includes a digital timing control circuit 84 configured to initiate a sequence for starting a time window each time the received voltage falls below the first threshold. The digital timing control circuit 84 is further configured to generate the enable signal, the enable signal transitioning between enable states in response to the received voltage crossing the second threshold. Each time window ends in response to a transition between enable states of the enable signal after the start of the time window. A duration of a time window is dependent upon a load of internal circuitry of the implanted medical device system 26. The internal coil interface 19 also includes switching circuitry 61 to connect the load to the rectified received voltage during a first time window and to disconnect the load from the rectified received voltage during a second time window.

According to this aspect, in some embodiments, the received voltage equals a voltage across internal circuitry of the medical device during the first and second time windows. In some embodiments, the first and second time windows are of unequal duration. In some embodiments, the first window is subsequent to the second window. In some embodiments, the load includes a load configured to be modulated to encode information concerning internal circuitry of the medical device 26. In some embodiments, modulation of the load affects a duration of a time window. In some embodiments, a change in the load affects a duration of a time window. In some embodiments, the duration of a time window increases when the load increases and the duration of the time window decreases when the load decreases. In some embodiments, the active rectifier circuit 78 delays switching rectifier states after the received voltage falls below the first threshold for a period of time, the period of time being dependent upon a duration of time the received voltage falls below the second threshold. In some embodiments, the delay in switching rectifier states increases when the rectifier switches state before the received voltage falls below the second threshold and the delay in switching rectifier states decreases when the rectifier switches states for an interval of time after the received voltage falls below the second threshold.

According to another embodiment, an internal coil interface 19 for a medical device 26 having an internal coil 18 and internal circuitry is provided. The internal coil interface 19 includes a first comparator 80 configured to determine when a time-vary periodic voltage received from the internal coil falls crosses a first threshold and a second comparator 82 configured to determine when the received voltage falls crosses a second threshold lower than the first threshold. The internal coil interface 19 includes a rectifier 78 configured to rectify the voltage received from the internal coil 18, the rectifier 78 switching between rectifier states in response to an enable signal. The internal coil interface 19 further includes digital timing control circuitry 84 configured to: estimate a first window of time for which the received voltage equals a voltage across the internal circuitry, the estimate being based at least in part on when the received voltage crosses the first threshold; and generate the enable signal for causing the rectifier 78 to switch between rectifier states based at least in part on when the received voltage falls below the second threshold. The internal coil interface 19 also includes switching circuitry 61 configured to connect a load to the rectified received voltage during the estimated first window of time.

According to this aspect, in some embodiments, the load is a load configured to be modulated to encode information concerning the internal circuitry to enable closed loop power regulation. In some embodiments, a duration of the estimated first window in time is based at least in part on modulation of the load. In some embodiments, the digital timing control circuitry 84 is further configured to estimate a second window of time for which the received voltage equals the voltage across the internal circuitry, and the switching circuitry 61 is further configured to disconnect a load to the rectified received voltage during the estimated second window of time for which the received voltage equals the voltage across the internal circuitry. In some embodiments, the rectifier 78 is configured to delay switching rectifier states for a first time interval in response to the received voltage falling below the first threshold. In some embodiments, when the delay causes the rectifier 78 to switch rectifier states after the received voltage falls below the second threshold, the delay is decreased. In some embodiments, when the delay causes the rectifier 78 to switch rectifier states before the received voltage falls below the second threshold, the delay is increased. In some embodiments, when the received voltage equals the voltage across the internal circuitry, power from the internal coil 18 is transmitted to the internal circuitry. In some embodiments, when the received voltage does not equal the voltage across the internal circuitry, current from the internal coil 18 is delivered to a tuning capacitor 104. In some embodiments, a change in the load affects a duration of the estimated first window of time. In some embodiments, the switching circuitry comprises NMOS type transistors 92, 96. In some embodiments, the load is a capacitance. In some embodiments, the estimate of the first window of time is based at least in part on whether a previous estimate of a time at which the received voltage will cross the first threshold is earlier or later than a time at which the crossing of the first threshold by the received voltage actually occurred.

According to yet another aspect, an internal coil interface 19 for an implanted medical device 26 having an internal coil 18 and internal circuitry is provided. The internal coil interface 19 includes a memory 60 configured to store timing information about when an internal coil voltage crosses voltage thresholds, the voltage threshold crossings defining successive windows. The memory 60 is also configured to store timing information about when a capacitance is switched into and out of a load modulation circuit 36 that modulates a load on the internal coil during each window. The timing information of an nth window of N successive windows after the capacitance is switched into or out of the load modulation circuit 36 at a first switching time is associated with the timing information of an nth window of N windows following each of M times that the capacitance is once again switched into or out of the load modulation circuit 36 to form a collection of M+1 sets of N windows, where n, N and M are each integers greater than zero. The internal coil interface 19 also includes processing circuitry 58 configured to: for each nth window in the collection of M+1 of the nth windows, predict a first predicted time of a first voltage level crossing of the internal coil voltage in the nth window after the capacitance is switched into or out of the load modulation circuit 36 for the (M+1)th time. When a time of switching the capacitance precedes the predicted time of the first voltage level crossing, then the internal coil interface 19 predicts that a voltage level crossing in an nth window after a next subsequent switching of the capacitance will occur earlier than the predicted time. When a time of switching the capacitance follows the predicted time of the first voltage level crossing, then the internal coil interface 19 predicts that a voltage level crossing of an nth window after a next subsequent switching of the capacitance will occur later than the predicted time.

According to another aspect, a method of timing the switching of a capacitance into or out of a modulated load circuit 36 in an internal coil interface 19 of an implanted medical device 26, the modulated load circuit 36 being modulated by the switching in order to communicate information from the implanted medical device to an external device via mutual coupling between an internal coil 18 and an external coil 20, is provided. The method includes predicting a time of a first voltage level crossing by a voltage at a terminal of the internal coil for each of a plurality of successive windows each time the capacitance is switched into the modulated load circuit 36 or each time the capacitance is switched out of the modulated load circuit 36. The method further includes adjusting the predictions based on whether a previous prediction of a time of a first voltage level crossing for a window was later or earlier than a time at which the first voltage level crossing actually occurred. In some embodiments, the digital timing circuitry 84 is further configured to estimate successive windows of time for which the received voltage equals a voltage across the internal circuitry in response to a system perturbation.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media and memory may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope of the invention, which is limited only by the following claims.

What is claimed is:

1. An internal coil interface for an implanted medical device having an internal coil, the internal coil interface configured to provide voltage rectification of a voltage received from the internal coil, the internal coil interface comprising:
    an active rectifier circuit configured to receive the voltage from the internal coil and switch rectifier states to rectify the voltage received from the internal coil, the switching being synchronized with an enable signal;
    a first comparator configured to receive the voltage from the internal coil and determine when the voltage received falls below a first threshold and to determine when the voltage received rises above the first threshold;
    a second comparator configured to receive the voltage from the internal coil and determine when the voltage received falls below a second threshold lower than the first threshold and to determine when the voltage received rises above the second threshold;
    a digital timing circuit coupled to the first comparator and the second comparator, the digital timing circuit configured to initiate a sequence for a starting of a time window each time the digital timing circuit receives a signal from the first comparator indicating the voltage received falls below the first threshold, the digital timing circuit being further configured to generate the enable signal, the enable signal transitioning between enable states in response to the digital timing circuit receiving another signal from the second comparator indicating the voltage received crossed the second threshold, each time window ending in response to a transition between enable states of the enable signal after the starting of the time window, a duration of the time window being dependent upon a load of internal circuitry of the implanted medical device; and
    switching circuitry to connect the load to the voltage rectified during a first time window and to disconnect the load from the voltage rectified during a second time window.

2. The internal coil interface of claim 1, wherein the voltage received equals a voltage across internal circuitry of the implanted medical device during the first and second time windows.

3. The internal coil interface of claim 1, wherein the first and second time windows are of unequal duration.

4. The internal coil interface of claim 1, wherein the first window is subsequent to the second window.

5. The internal coil interface of claim 1, wherein the load includes a load configured to be modulated to encode information concerning internal circuitry of the implanted medical device.

6. The internal coil interface of claim 5, wherein modulation of the load affects the duration of the time window.

7. The internal coil interface of claim 1, wherein a change in the load affects the duration of the time window.

8. The internal coil interface of claim 7, wherein, the duration of the time window increases when the load increases and the duration of the time window decreases when the load decreases.

9. The internal coil interface of claim 1, wherein the active rectifier circuit delays switching rectifier states after the voltage received falls below the first threshold for a period of time, the period of time being dependent upon a duration of time the voltage received falls below the second threshold.

10. The internal coil interface of claim 9, wherein the delay in switching rectifier states increases when the active rectifier circuit switches state before the voltage received falls below the second threshold and the delay in switching rectifier states decreases when the active rectifier circuit switches states for an interval of time after the voltage received falls below the second threshold.

11. An internal coil interface for a medical device having an internal coil and internal circuitry, the internal coil interface comprising:
    a first comparator configured to receive a time-varying periodic voltage from the internal coil and determine when the time-varying periodic voltage received from the internal coil crosses a first threshold;
    a second comparator configured to receive the time-varying periodic voltage from the internal coil and determine when the time-varying periodic voltage received from the internal coil falls below a second threshold lower than the first threshold;
    a rectifier configured to rectify the time-varying periodic voltage received from the internal coil, the rectifier switching between rectifier states in response to an enable signal; and
    a digital timing circuitry configured to:
        estimate a first window of time for which the time-varying periodic voltage received from the internal coil equals a voltage across the internal circuitry, the estimate being based at least in part on when the time-varying periodic voltage received from the internal coil crosses the first threshold; and
        generate the enable signal for causing the rectifier to switch between rectifier states based at least in part on when the time-varying periodic voltage received from the internal coil falls below the second threshold; and
    switching circuitry configured to connect a load to the time-varying periodic voltage rectified during the estimated first window of time.

12. The internal coil interface of claim 11, wherein the load is a load configured to be modulated to encode information concerning the internal circuitry to enable closed loop power regulation.

13. The internal coil interface of claim 12, wherein a duration of the estimated first window in time is based at least in part on modulation of the load.

14. The internal coil interface of claim 11, wherein:
    the digital timing circuitry is further configured to estimate a second window of time for which the time-varying periodic voltage received from the internal coil equals the voltage across the internal circuitry; and
    the switching circuitry is further configured to disconnect a load to the time-varying periodic voltage rectified during the estimated second window of time for which the time-varying periodic voltage received from the internal coil equals the voltage across the internal circuitry.

15. The internal coil interface of claim 11, wherein the rectifier is configured to delay switching rectifier states for a first time interval—in response to the time-varying periodic voltage received from the internal coil falling below the first threshold.

16. The internal coil interface of claim 15, wherein, when the delay causes the rectifier to switch rectifier states after the time-varying periodic voltage received from the internal coil falls below the second threshold, the delay is decreased.

17. The internal coil interface of claim 15, wherein, when the delay causes the rectifier to switch rectifier states before the time-varying periodic voltage received from the internal coil falls below the second threshold, the delay is increased.

18. The internal coil interface of claim 11, wherein, when the time-varying periodic voltage received from the internal coil equals the voltage across the internal circuitry, power from the internal coil is transmitted to the internal circuitry.

19. The internal coil interface of claim 11, wherein, when the time-varying periodic voltage received from the internal coil does not equal the voltage across the internal circuitry, current from the internal coil is delivered to a tuning capacitor.

20. The internal coil interface of claim 11, wherein the digital timing circuitry is further configured to estimate successive windows of time for which the time-varying periodic voltage received from the internal coil equals the voltage across the internal circuitry in response to a system perturbation.

\* \* \* \* \*